United States Patent
Barbato et al.

(10) Patent No.: US 9,883,840 B2
(45) Date of Patent: *Feb. 6, 2018

(54) DYNAMICALLY SCANNED X-RAY DETECTOR PANEL

(71) Applicant: Medtronic Navigation, Inc., Louisville, CO (US)

(72) Inventors: Louis J. Barbato, Franklin, MA (US); Patrick A. Helm, Milton, MA (US); Jigney Shah, Ashland, MA (US)

(73) Assignee: Medtronic Navigation, Inc., Louisville, CO (US)

(*) Notice: Subject to any disclaimer, the term of this patent is extended or adjusted under 35 U.S.C. 154(b) by 21 days.

This patent is subject to a terminal disclaimer.

(21) Appl. No.: 14/611,509

(22) Filed: Feb. 2, 2015

(65) Prior Publication Data

US 2015/0146854 A1 May 28, 2015

Related U.S. Application Data

(63) Continuation of application No. 13/288,456, filed on Nov. 3, 2011, now Pat. No. 8,948,338.

(51) Int. Cl.
*A61B 6/03* (2006.01)
*G01T 1/20* (2006.01)
(Continued)

(52) U.S. Cl.
CPC .......... *A61B 6/4208* (2013.01); *A61B 6/032* (2013.01); *A61B 6/4233* (2013.01);
(Continued)

(58) Field of Classification Search
CPC ..... G01T 1/2018; G01T 1/2964; A61B 6/032; A61B 6/4208; A61B 6/4233
(Continued)

(56) References Cited

U.S. PATENT DOCUMENTS 4,593,400 A 6/1986 Mouyen
5,463,216 A * 10/1995 Van Berkel ....... H01L 27/14603
250/208.1
(Continued)

FOREIGN PATENT DOCUMENTS

CN 101357066 A 2/2009
CN 102460703 A 5/2012
(Continued)

OTHER PUBLICATIONS

Arda D Yalcinkaya, et al., "NiFe Plated Biaxial MEMS Scanner for 2-D Imaging," IEEE Photonics Technology Letters, IEEE Service Center, Piscataway, NJ, US, vol. 19, No. 5, (Mar. 2007). pp. 330-332.
(Continued)

*Primary Examiner* — Allen C. Ho
(74) *Attorney, Agent, or Firm* — Harness Dickey (57) ABSTRACT

An x-ray imaging system for imaging a subject includes an x-ray source configured to project an x-ray radiation toward a portion of the subject and a panel detector positioned opposite the x-ray source relative to the subject and configured to receive x-ray radiation passing through the subject. The panel detector includes a scintillation layer converting x-ray radiation to light rays of a selected spectrum and a plurality of microelectromechanical scanners. Each microelectromechanical scanner includes a photodetector mounted on a corresponding movable platform and configured to detect light in the selected light spectrum. The panel detector includes a scanning control module configured to move each platform in a selected scan pattern.

35 Claims, 6 Drawing Sheets

(51) Int. Cl.
*G01T 1/29* (2006.01)
*A61B 6/00* (2006.01)
*G01N 23/04* (2006.01)

(52) U.S. Cl.
CPC .......... *G01T 1/2018* (2013.01); *G01T 1/2964* (2013.01); *G01N 23/04* (2013.01)

(58) Field of Classification Search
USPC .............................. 378/19, 98.8; 250/370.09
See application file for complete search history.

(56) References Cited

U.S. PATENT DOCUMENTS

| | | | |
|---|---|---|---|
| 5,864,146 A * | 1/1999 | Karellas | A61B 6/4258 250/581 |
| 6,215,848 B1 * | 4/2001 | Linders | A61B 6/481 250/370.09 |
| 6,292,534 B1 * | 9/2001 | Linders | A61B 6/4233 348/E5.086 |
| 6,600,158 B1 | 7/2003 | Okada et al. | |
| 6,710,350 B2 | 3/2004 | Ruzga | |
| 6,920,203 B2 | 7/2005 | Short et al. | |
| 6,940,941 B2 | 9/2005 | Gregerson et al. | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,135,686 B1 * | 11/2006 | Grady | G01T 1/2018 250/370.11 |
| 7,188,998 B2 | 3/2007 | Gregerson et al. | |
| 7,595,819 B2 | 9/2009 | Kondo | |
| 8,238,631 B2 | 8/2012 | Hartmann et al. | |
| 8,624,187 B2 | 1/2014 | Urey et al. | |
| 8,737,567 B2 * | 5/2014 | Shah | A61B 6/405 378/95 |
| 8,948,338 B2 | 2/2015 | Barbato et al. | |
| 8,971,495 B2 * | 3/2015 | Shah | A61B 6/032 378/101 |
| 2003/0130562 A1 | 7/2003 | Barbato et al. | |
| 2003/0168603 A1 | 9/2003 | Ruzga | |
| 2010/0290690 A1 | 11/2010 | Hartmann et al. | |
| 2013/0114789 A1 | 5/2013 | Barbato et al. | |
| 2015/0098549 A1 * | 4/2015 | Humphrey | A61B 6/4208 378/62 |

FOREIGN PATENT DOCUMENTS

| | | |
|---|---|---|
| JP | 2005051638 A | 2/2005 |
| JP | 2007-136050 A | 6/2007 |
| JP | 2012-090770 A | 5/2012 |

OTHER PUBLICATIONS

International Preliminary Report on Patentability and Written Opinion for PCT/US2012/062577 dated May 15, 2014 claiming benefit of U.S. Appl. No. 13/288,456, filed Nov. 3, 2011.

International Search Report and Written Opinion for PCT/US2012/062577 dated Apr. 16, 2013 claiming benefit of U.S. Appl. No. 13/288,456, filed Nov. 3, 2011.

Japanese Office Action dated Jun. 15, 2015 for Japan Patent Application No. 2014-540014, claiming priority from U.S. Appl. No. 13/288,456, filed Nov. 3, 2011.

Chinese Office Action dated Oct. 10, 2015 for Chinese Patent Application No. 201280065723.9, claiming priority from U.S. Appl. No. 13/288,456, filed Nov. 3, 2011.

Japanese Office Action dated Mar. 24, 2017 for Japanese Application No. 2016-078711, claiming priority from Japanese Application No. 2014-540014, claiming priority to PCT/US2012/062577, claiming priority from U.S. Appl. No. 13/288,456, filed Nov. 3, 2011.

Communication pursuant to Article 94(3) EPC dated Jan. 25, 2017 for European Application No. 127989101 f corresponding to PCT/US2012/062577 claiming benefit of U.S. Appl. No. 13/288,456, filed Nov. 3, 2011.

Australian Office Action dated Feb. 7, 2017 for Australian Application No. 2016203239 corresponding to PCT/US2012/062577 claiming benefit of U.S. Appl. No. 13/288,456, filed Nov. 3, 2011.

* cited by examiner

DYNAMICALLY SCANNED X-RAY DETECTOR PANEL

CROSS-REFERENCE TO RELATED APPLICATIONS

This application is a continuation of U.S. patent application Ser. No. 13/288,456 filed on Nov. 3, 2011 (now U.S. Pat. No. 8,948,338 B2, issued on Feb. 3, 2015). The entire disclosure of the above application is incorporated herein by reference.

FIELD

The present disclosure relates to generating an image of subject using an imaging system having a flat panel detector and more specifically, a dynamically scanned x-ray detector.

BACKGROUND

This section provides background information related to the present disclosure which is not necessarily prior art.

A subject, such as a human patient, may select or be required to undergo a surgical procedure to correct or augment an anatomy of the patient. The augmentation of the anatomy can include various procedures, such as movement or augmentation of bone, insertion of implantable devices, or other appropriate procedures. A surgeon can perform the procedure on the subject with images of the patient that can be acquired using imaging systems such as a magnetic resonance imaging (MRI) system, computed tomography (CT) system, fluoroscopy (e.g., C-Arm imaging systems), or other appropriate imaging systems.

Images of a patient can assist a surgeon in performing a procedure including planning the procedure and performing the procedure. A surgeon may select a two dimensional image or a three dimensional image representation of the patient. The images can assist the surgeon in performing a procedure with a less invasive technique by allowing the surgeon to view the anatomy of the patient without removing the overlying tissue (including dermal and muscular tissue) when performing a procedure.

SUMMARY

This section provides a general summary of the disclosure, and is not a comprehensive disclosure of its full scope or all of its features.

The present teachings provide an x-ray imaging system for imaging a subject includes an x-ray source configured to project an x-ray radiation toward a portion of the subject and a panel detector positioned opposite the x-ray source relative to the subject and configured to receive x-ray radiation passing through the subject. The panel detector includes a scintillating layer converting x-ray radiation to light rays of a selected spectrum and a plurality of microelectromechanical scanners. Each microelectromechanical scanner includes a photodetector mounted on a corresponding movable platform and configured to detect light in the selected light spectrum. The panel detector includes a scanning control module configured to move each platform in a selected scan pattern.

The present teachings also provide a method of x-ray imaging that includes providing a panel detector including a scintillation layer deposited on a glass layer and a plurality of microelectromechanical scanners. Each microelectromechanical scanner includes a photodetector mounted on a movable platform. The method further includes positioning a subject between an x-ray source and the panel detector, directing x-ray radiation emitted from the x-ray source to the scintillation layer, and directing light rays emitted from the scintillation layer toward the microelectromechanical scanners. Each microelectromechanical scanner is controlled to scan a corresponding area of the scintillation layer in an individually selectable scanning pattern. The scanning patterns are processed and an image of a portion of the subject is created.

In some embodiments, the microelectromechanical scanners can include different photodetectors with photodiodes or mirrors and electrocoil. The platform can be pivotable using flexible actuators.

In some embodiments, adjacent microelectromechanical scanners can be positioned to have overlapping fields of view.

In some embodiments the scanning patterns can include rectangular raster scanners with individually selectable frequencies. In some embodiments the scanning patterns can include spiral scans.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

The following description is merely exemplary in nature. It should be understood that throughout the drawings, corresponding reference numerals indicate like or corresponding parts and features. As indicated above, the present teachings are directed toward an imaging system, such as an O-Arm® imaging system commercially available from Medtronic Navigation, Inc., Louisville, Colo., USA. It should be noted, however, that the present teachings could be applicable to any appropriate imaging device, such as a C-arm imaging device. Further, as used herein, the term "module" can refer to a computer readable media that can be accessed by a computing device, an application specific integrated circuit (ASIC), an electronic circuit, a processor (shared, dedicated, or group) and memory that executes one or more software or firmware programs, a combinational logic circuit, and/or other suitable software, firmware programs or components that provide the described functionality.

The present teachings are directed to various embodiments of a dynamically scanned flat panel detector for an imaging system used in medical imaging, such as, for example, radiography, fluoroscopy, computed tomography (CT) and cone beam computed tomography (CBCT). The flat panel detector of the present teachings incorporates a plurality of individual micro-scanners (including photodetectors) that can scan one portion of area of interest according to an individually-selected raster pattern. Each scanned portion contributes to a portion of the overall image, which is then stitched together from the separate portion. In comparison to some prior art flat panel detectors that include photodetector arrays in a regular and fixed grid pattern, the flat panel detector of the present teachings provides additional flexibility and efficiency in controlling resolution, sampling rate, image processing, cost reduction, calibration, etc., by individually controlling the scanning patterns, types and locations of the photodetectors included in the individual micro-scanners. The micro-scanners included in the flat panel detector of the present teachings can be arranged in rows and columns ((two-dimensional array) and are based on microelectromechanical systems (MEMS) principles. Scanning motion can be in a preselected pattern resulting in spiral, radial, circular or rectangular raster pattern of different sweep frequencies. The micro-scanners can be actuated, for example, by using x and y mechanical actuators for pivoting corresponding photodiodes about two orthogonal axes or by using electrocoils and magnets to pivot MEMS mirrors about two orthogonal axes.

Figure 1:
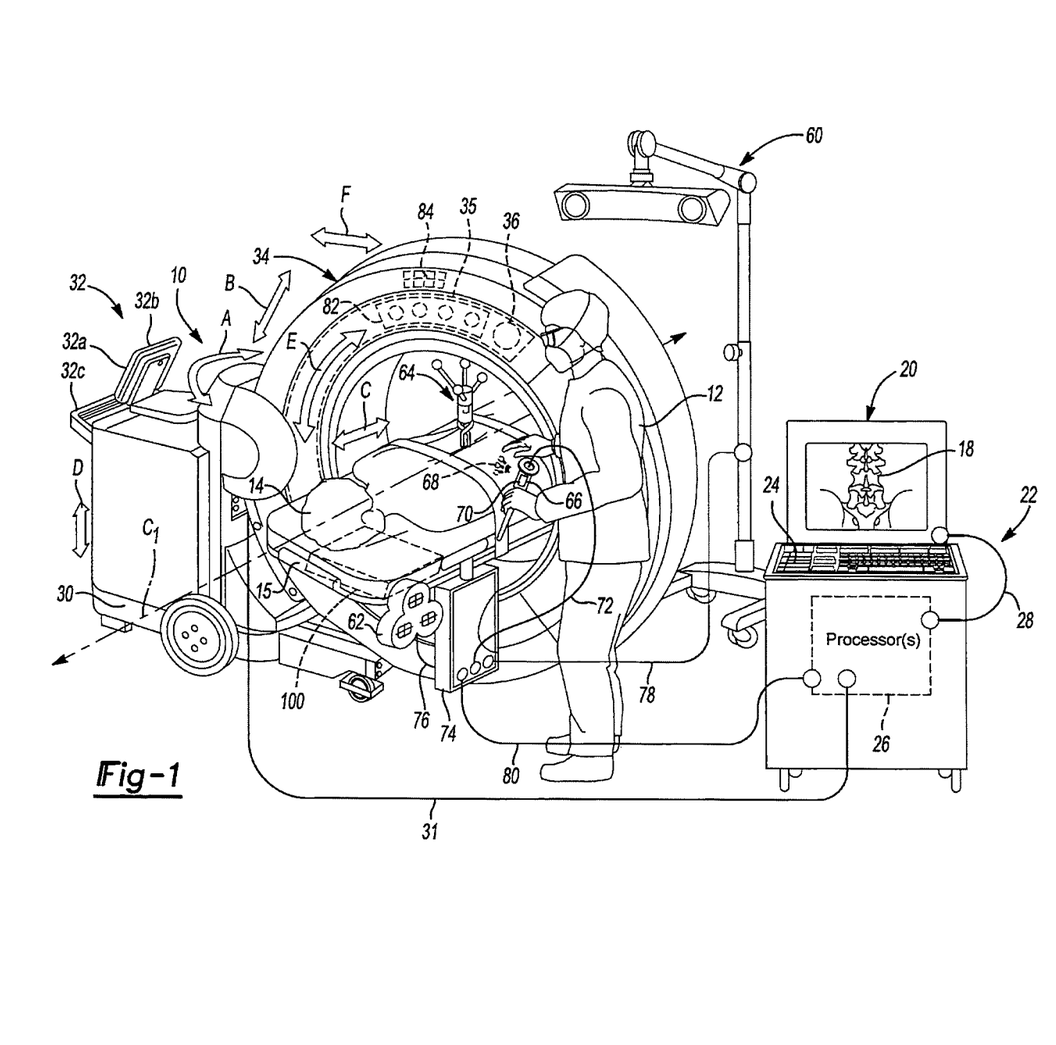
FIG. 1 is an environmental view of an exemplary imaging system including a flat panel detector according to the present teachings.
Figure 2:
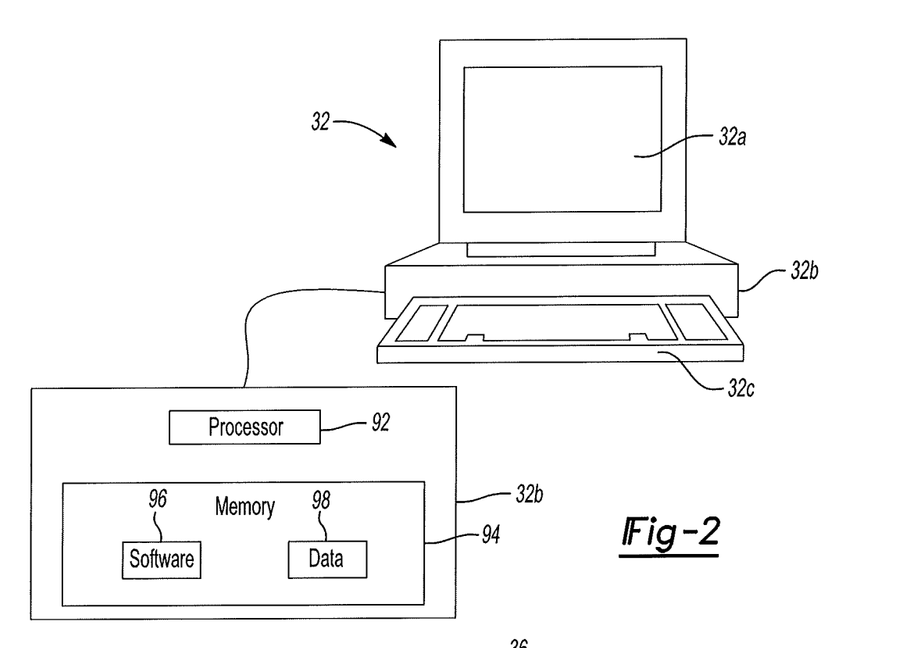
FIG. 2 is an exemplary computer system in use with the imaging system of FIG. 1.
Figure 3:
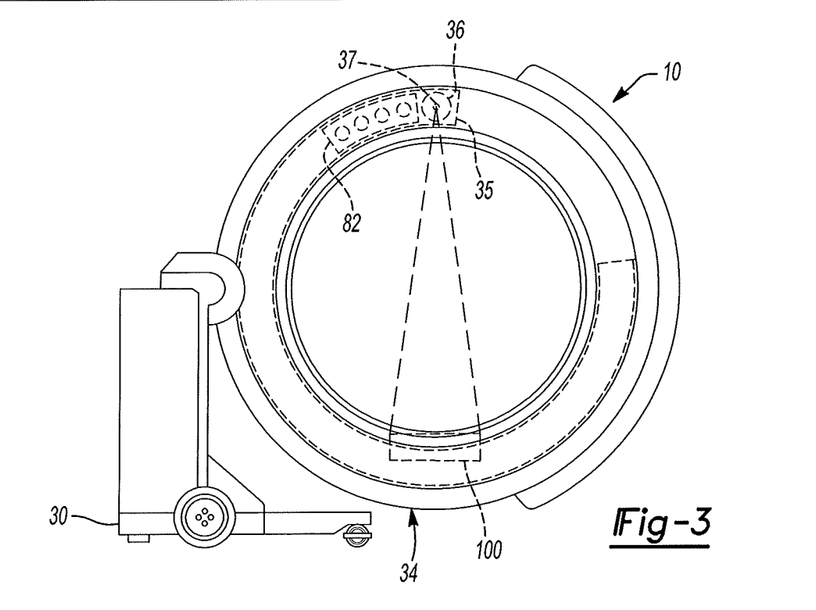
FIG. 3 is a schematic illustration of an x-ray source of the imaging system of FIG. 1 shown in alignment with the flat panel detector.
Figure 4A:
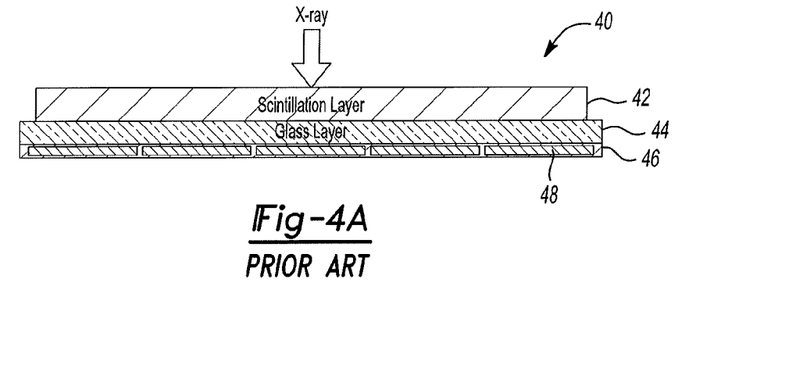
FIG. 4A is a schematic side sectional view of a prior art flat panel detector.
Figure 4B:
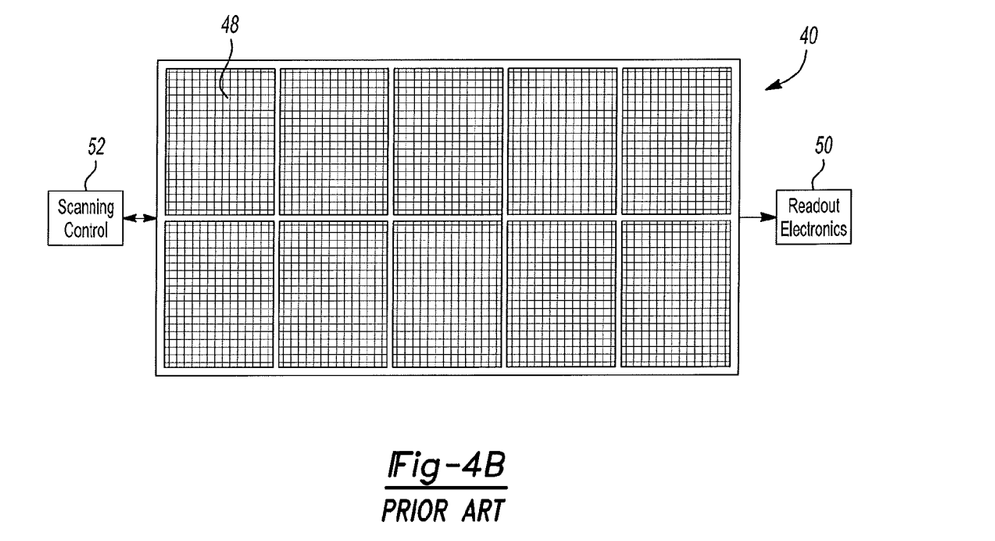
FIG. 4B is a schematic plan view of the prior art flat panel detector of FIG. 4A.
Figure 9:
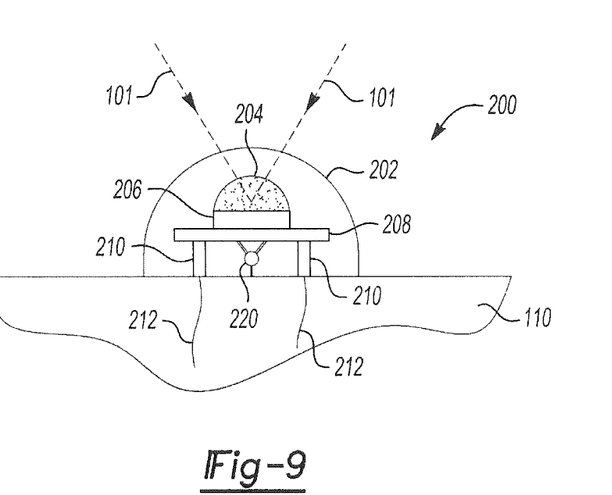
FIG. 9 is a schematic side sectional view of an exemplary micro-scanner device for a flat panel detector according to the present teachings.
Figure 10:
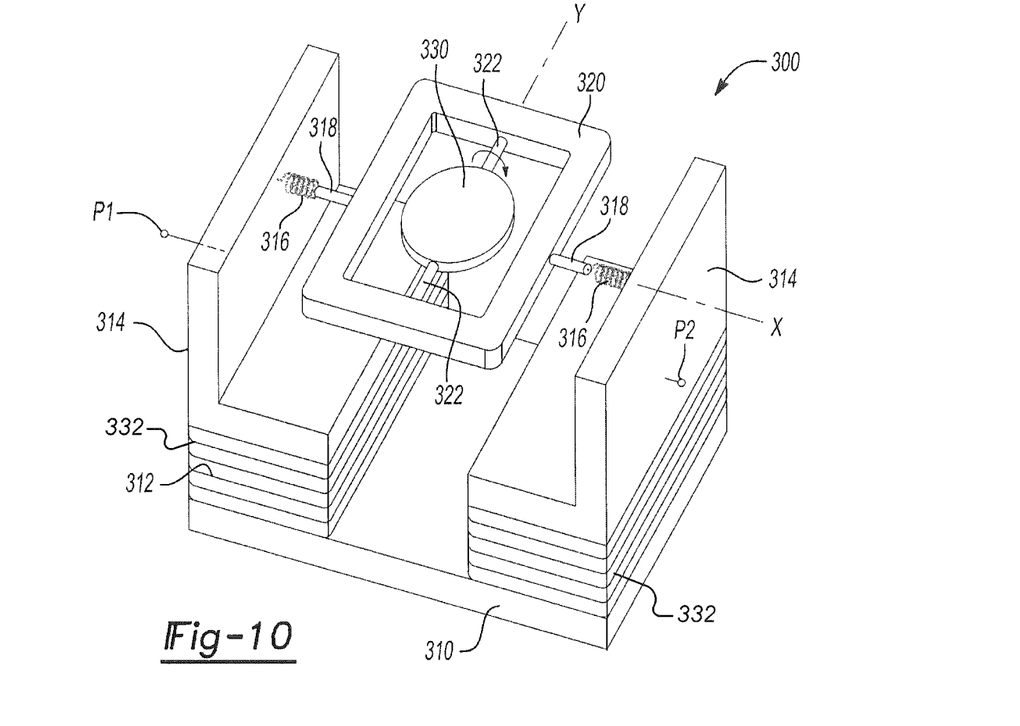
FIG. 10 is a schematic perspective view of another exemplary micro-scanner device for a flat panel detector according to the present teachings.

Briefly, FIGS. 1-3 illustrate various components of an exemplary CBCT imaging system 10. FIGS. 4A and 4B illustrate a prior art flat panel detector 40. FIGS. 5-8 illustrate various embodiments of a MEMS-based flat panel detector 100, 100a, 100b, 100c according to the present teachings. FIG. 9 illustrates a micro scanner 200 with a photodiode and x, y actuators for pivoting. FIG. 10 illustrates a micro-scanner 300 with a mirror using magnetic field actuation.

With reference to FIG. 1, a user 12, such as a medical professional or assistant, can perform a procedure on a subject, such as a human patient 14. In performing the procedure, the user 12 can use an imaging system 10 to acquire image data of the patient 14 for performing a procedure. The image data acquired of the patient 14 can include two-dimensional (2D) projections acquired with an x-ray imaging system, including those disclosed herein. It will be understood, however, that 2D forward projections of a volumetric model can also be generated, also as disclosed herein.

In one example, a model can be generated using the acquired image data. The model can be a three-dimensional (3D) volumetric model generated based on the acquired image data using various techniques, including algebraic iterative techniques, to generate image data displayable on a display, referenced as displayed image data 18. Displayed image data 18 can be displayed on a display device 20, and additionally, can be displayed on a display device 32a associated with an imaging computing system 32. The displayed image data 18 can be a 2D image, a 3D image, or a time changing four-dimensional image. The displayed image data 18 can also include the acquired image data, the generated image data, both, or a merging of both types of image data.

It will be understood that the image data acquired of the patient 14 can be acquired as 2D projections, for example with an x-ray imaging system. The 2D projections can then be used to reconstruct the 3D volumetric image data of the patient 14. Also, theoretical or forward 2D projections can be generated from the 3D volumetric image data. Accordingly, it will be understood that image data can be either or both of 2D projections or 3D volumetric models.

The display device 20 can be part of a computing system 22. The computing system 22 can include a variety of computer-readable media. The computer-readable media can be any available media that can be accessed by the computing system 22 and can include both volatile and non-volatile media, and removable and non-removable media. The computer-readable media can include, for example, computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 22. The computer-readable media may be accessed directly or through a network such as the Internet.

In one example, the computing system 22 can include an input device 24, such as a keyboard, and one or more processors 26 (the one or more processors can include multiple-processing core processors, microprocessors, etc.) that can be incorporated with the computing system 22. The input device 24 can include any suitable device to enable a user to interface with the computing system 22, such as a touchpad, touch pen, touch screen, keyboard, mouse, joystick, trackball, wireless mouse, audible control or a combination thereof. Furthermore, while the computing system 22 is described and illustrated herein as comprising the input device 24 discrete from the display device 20, the computing system 22 could comprise a touchpad or tablet computing device, and further, the computing system 22 could be integrated within or be part of the imaging computing system 32 associated with the imaging system 10. A wired or wireless connection 28 can be provided between the computing system 22 and the display device 20 for data communication to allow driving the display device 20 to illustrate the image data 18.

The imaging system 10, including the O-Arm® imaging system, or other appropriate imaging systems in use during a selected procedure are also described in U.S. patent application Ser. No. 12/465,206, entitled "System And Method For Automatic Registration Between An Image And A Subject," filed on May 13, 2009, U.S. Publication No. 2010-0290690, issued on Nov. 18, 2010, and U.S. Pat. No. 8,238,631, issued on Aug. 7, 2012, which are incorporated herein by reference. Additional description regarding the O-Arm imaging system or other appropriate imaging systems can be found in U.S. Pat. Nos. 8,238,631, 7,188,998, 7,108,421, 7,106,825, 7,001,045 and 6,940,941, each of which is incorporated herein by reference.

Referring to FIGS. 1-8, the imaging system 10 can include a mobile cart 30 that includes the imaging computing system 32 and an imaging gantry 34 with a source 36, a collimator 37, one of the flat panel detectors 100, 100a, 100b, 100c of the present teachings and a rotor 35. For simplicity, the flat panel detector 100 is referenced in connection with FIGS. 1-3, although any of the other embodiments 100a, 100b, and 100c can be also used. With reference to FIG. 1, the mobile cart 30 can be moved from one operating theater or room to another and the gantry 34 can move relative to the mobile cart 30, as discussed further herein. This allows the imaging system 10 to be mobile so that it can be used in multiple locations and with multiple procedures without requiring a capital expenditure or space dedicated to a fixed imaging system.

With continued reference to FIG. 1, the gantry 34 can define an isocenter of the imaging system 10. In this regard, a centerline C1 through the gantry 34 can define an isocenter or center of the imaging system 10. Generally, the patient 14 can be positioned along the centerline C1 of the gantry 34, so that a longitudinal axis of the patient 14 can be aligned with the isocenter of the imaging system 10.

With reference to FIG. 2, a diagram is provided that illustrates an exemplary embodiment of the imaging computing system 32, some or all of the components of which can be used in conjunction with the teachings of the present disclosure. The imaging computing system 32 can include a variety of computer-readable media. The computer-readable media can be any available media that can be accessed by the imaging computing system 32 and includes both volatile and non-volatile media, and removable and non-removable media. By way of example, and not limitation, the computer-readable media can comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the imaging computing system 32. The computer-readable media may be accessed directly or through a network such as the Internet.

In one example, the imaging computing system 32 comprises a display device 32a and a system unit 32b. As illustrated, the display device 32a can comprise a computer video screen or monitor. The imaging computing system 32 can also include at least one input device 32c. The system unit 32b includes, as shown in an exploded view, a processor 92 and a memory 94, which can include software with an image control module 96 and data 98, as shown in FIG. 2.

In this example, the at least one input device 32c comprises a keyboard. It should be understood, however, that the at least one input device 32c can comprise any suitable device to enable a user to interface with the imaging computing system 32, such as a touchpad, touch pen, touch screen, keyboard, mouse, joystick, trackball, wireless mouse, audible control or a combination thereof. Furthermore, while the imaging computing system 32 is described and illustrated herein as comprising the system unit 32b with the display device 32a, the imaging computing system 32 could comprise a touchpad or tablet computing device or use display device 20.

Briefly, with reference to FIGS. 1 and 3, the source 36 can emit x-rays through the patient 14 to be detected by the flat panel detector 100. The x-rays can be emitted by the source 36 in a cone beam and can be further shaped by an optional collimator 37 for detection by the flat panel detector 100. An exemplary collimator 37 is commercially available as the Compact Square Field Collimator sold by Collimare Engineering of Wheat Ridge, Colo., USA and included with the O-Arm® imaging system sold by Medtronic Navigation, Inc. of Louisville, Colo., USA. Briefly, the collimator 37 can include one or more leaves, which can be controlled to shape the x-rays emitted by the source 36. As will be discussed, the collimator 37 can be used to shape the x-rays emitted by the source 36 into a beam that corresponds with the shape of the flat panel detector 100. The source 36, collimator 37 and the flat panel detector 100 can each be coupled to the rotor 35.

Generally, the flat panel detector 100 can be coupled to the rotor 35 so as to be diametrically opposed from the source 36 and the collimator 37 within the gantry 34. The flat panel detector 100 can move rotationally in a 360° motion around the patient 14 generally in the directions of arrow E, and the source 36 and collimator 37 can move in concert with flat panel detector 100 such that the source 36 and collimator 37 remain generally 180° apart from and opposed to the flat panel detector 100.

The gantry 34 can isometrically sway or swing (herein also referred to as iso-sway) generally in the direction of arrow A, relative to the patient 14, which can be placed on a patient support or table 15. The gantry 34 can also tilt relative to the patient 14, as illustrated by arrows B, move longitudinally along the line C relative to the patient 14 and the mobile cart 30, can move up and down generally along the line D relative to the mobile cart 30 and transversely to the patient 14, and move perpendicularly generally in the direction of arrow F relative to the patient 14 to allow for positioning of the source 36, collimator 37 and flat panel detector 100 relative to the patient 14.

The imaging system 10 can be precisely controlled by the imaging computing system 32 to move the source 36, collimator 37 and the flat panel detector 100 relative to the patient 14 to generate precise image data 18 of the patient 14. In addition, the imaging system 10 can be connected with the processor 26 via connection 31 which can include a wired or wireless connection or physical media transfer from the imaging system 10 to the processor 26. Thus, image data 18 collected with the imaging system 10 can also be transferred from the imaging computing system 32 to the computing system 22 for navigation, display, reconstruction, etc.

Briefly, with continued reference to FIG. 1, according to various embodiments, the imaging system 10 can be used with an unnavigated or navigated procedure. In a navigated procedure, a localizer, including either or both of an optical localizer 60 and an electromagnetic localizer 62 can be used to generate a field or receive or send a signal within a navigation domain relative to the patient 14. If desired, the components associated with performing a navigated procedure could be integrated within the imaging system 10. The navigated space or navigational domain relative to the patient 14 can be registered to the image data 18 to allow registration of a navigation space defined within the navigational domain and an image space defined by the image data 18. A patient tracker or a dynamic reference frame 64 can be connected to the patient 14 to allow for a dynamic registration and maintenance of registration of the patient 14 to the image data 18.

An instrument 66 can then be tracked relative to the patient 14 to allow for a navigated procedure. The instrument 66 can include an optical tracking device 68 and/or an electromagnetic tracking device 70 to allow for tracking of the instrument 66 with either or both of the optical localizer 60 or the electromagnetic localizer 62. The instrument 66 can include a communication line 72 with a navigation interface device 74, which can communicate with the electromagnetic localizer 62 with a communication line 76 and/or the optical localizer 60 with a communication line 78. The navigation interface device 74 communicates with the processor 26 via a communication line 80. It will be understood that any of the connections or communication lines 28, 31, 76, 78, or 80 can be wired, wireless, physical media transmission or movement, or any other appropriate communication. Nevertheless, the appropriate communication systems can be provided with the respective localizers to allow for tracking of the instrument 66 relative to the patient 14 to allow for illustration of the tracked location of the instrument 66 relative to the image data 18 for performing a procedure.

It will be understood that the instrument 66 can be an interventional instrument and/or an implant. Implants can include a ventricular or vascular stent, a spinal implant, neurological stent or the like. The instrument 66 can be an interventional instrument such as a deep brain or neurological stimulator, an ablation device, or other appropriate instrument. Tracking the instrument 66 allows for viewing the location of the instrument 66 relative to the patient 14 with use of the registered image data 18 and without direct viewing of the instrument 66 within the patient 14. For example, the instrument 66 could be graphically illustrated as an icon superimposed on the image data 18.

Further, the imaging system 10 can include a tracking device, such as an optical tracking device 82 or an electromagnetic tracking device 84 to be tracked with a respective optical localizer 60 or the electromagnetic localizer 62. The tracking device 82, 84 can be associated directly with the source 36, the flat panel detector 100, rotor 35, the gantry 34, or other appropriate part of the imaging system 10 to determine the location or position of the source 36, the flat panel detector 100, rotor 35 and/or gantry 34 relative to a selected reference frame. As illustrated, the tracking device 82, 84 can be positioned on the exterior of the housing of the gantry 34. Accordingly, the imaging system 10 can be tracked relative to the patient 14, as can the instrument 66 to allow for initial registration, automatic registration or continued registration of the patient 14 relative to the image data 18. Registration and navigated procedures are discussed in the above incorporated U.S. patent application Ser. No. 12/465,206, filed on May 13, 2009 and in U.S. Pat. No. 8,238,631.

In one example, the image data 18 can comprise a single 2D image. In another example, the image control module 96 can perform automatic reconstruction of an initial three dimensional model of the area of interest of the patient 14. Reconstruction of the three dimensional model can be performed in any appropriate manner, such as using algebraic techniques for optimization. Appropriate algebraic techniques include Expectation maximization (EM), Ordered Subsets EM (OS-EM), Simultaneous Algebraic Reconstruction Technique (SART) and total variation minimization. The application to performing a 3D volumetric reconstruction based on the 2D projections allows for efficient and complete volumetric reconstruction.

Generally, an algebraic technique can include an iterative process to perform a reconstruction of the patient 14 for display as the image data 18. For example, a pure or theoretical image data projection, such as those based on or generated from an atlas or stylized model of a "theoretical" patient, can be iteratively changed until the theoretical projection images match the acquired 2D projection image data of the patient 14. Then, the stylized model can be appropriately altered as the 3D volumetric reconstruction model of the acquired 2D projection image data of the selected patient 14 and can be used in a surgical intervention, such as navigation, diagnosis, or planning. In this regard, the stylized model can provide additional detail regarding the anatomy of the patient 14, which can enable the user to plan the surgical intervention much more efficiently. The theoretical model can be associated with theoretical image data to construct the theoretical model. In this way, the theoretical model or the theoretical image data can be built based upon image data 18 acquired of the patient 14 with the imaging system 10. The image control module 96 can output image data 18 to the display device 32a.

Referring to FIGS. 4A and 4B, an exemplary prior art flat panel detector 40 is illustrated diagrammatically. The flat panel detector 40 can include a scintillation layer 42 positioned to receive x-rays from an x-ray source such as source 36 in FIG. 3 (after passing through the subject 14), and a glass layer 44 that includes an electronic layer 46. The scintillation layer 42 is a layer of scintillation material deposited directly on the glass layer 44. The scintillation layer 42 can be, for example, a gadolinium oxysulfite layer or a cesium iodide (CsI) layer. The electronics layer 46 can include an array of Application Specific Integrated Circuits (ASICS), such as an array of Thin Film Transistors (TFTs) 48 and is connected to a scanning control module 52 and a readout module 50. More specifically, the scintillation layer 42 is positioned to receive incident x-rays from an x-ray source (through the subject) and converts the x-rays to light photons or light rays that pass through the glass layer 44. The glass layer 44 can be coated with amorphous silicon imprinted with a multitude of TFTs 48 arranged in a regular grid of rows and columns (shown in FIG. 4B) that is part of the electronics layer 46. Each of the TFTs 48 is attached to a photodiode that corresponds to an individual pixel (picture element). The photons that strike the photodiodes in the TFTs 48 have variable intensity and are converted to electrical signals, such as an electrical charge (electrons) that are stored in the capacitance of the photodiodes and create an electrical pattern corresponding to the variable intensity of photons. The TFTs/photodiodes 48 are scanned progressively one line at a time (such as a row or column) in one direction using the scanning control module 52. The TFTs 48 act as switches that discharge the stored electron charge from each pixel in a selected row (or column) to a dataline coupled to the readout module 50. At the end of each dataline, an amplifier can convert the electron charge to voltage. The readout module 50 can include a programmable gain stage and an analog-to digital converter (ADC) that converts the voltage to a digital number that can produce a digital image in a computer display. It is noted that in the prior art flat panel detector 40, the ASICS are aligned on a grid and create an area of light collecting pixels that have a fixed size.

In contrast to the prior art flat panel detector 40, the present teachings provide various MEMS flat panel detectors 100, 100a, 100b, 100c (FIGS. 5-8) that use microscanners or MEMS scanners 106 including photodetectors with a narrow acceptance angle such that each photodetector collects light from a small area of the scintillation layer, such that calibration, scanning pattern and sampling rate can be controlled for each MEMS scanner 106. Each area scanned by a corresponding MEMS scanner produces a block of an image and the entire image is created by stitching these blocks as in the prior art flat panel detectors 40. Some of the areas of interest of the scintillation layer 42 can be scanned by two (or more) MEMS scanners with overlapping fields of view. The MEMS scanners can include linear actuators and pivoters and can allow, for example rectangularly-shaped scan raster patterns 122a, 122b, 122c of variable sweep frequencies, spiral raster patterns 120 or other raster patterns, as shown in FIG. 5B.

Figure 5A:
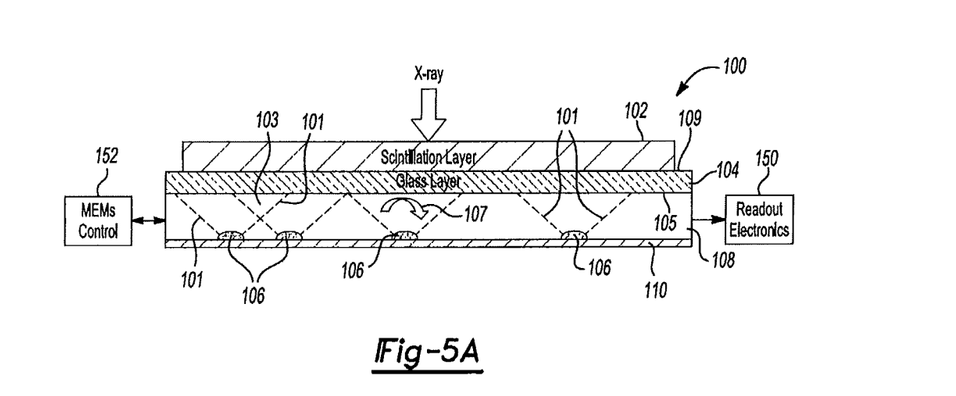
FIG. 5A is a schematic side sectional view of a flat panel detector according to the present teachings.
Figure 5B:
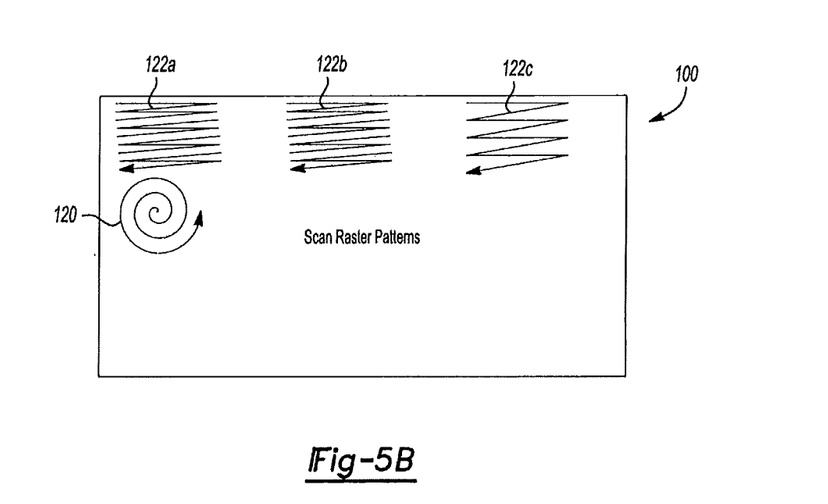
FIG. 5B is a schematic plan view of the flat panel detector of FIG. 5A showing exemplary raster patterns.

Referring to FIG. 5A, the MEMS flat panel detector 100 of the present teachings includes a scintillation layer 102 and a glass layer 104 having an inner surface 105 and an outer surface 109. The scintillation layer 102 receives x-rays passing through a subject and scintillates to produce light in a particular spectrum through the glass layer 104. The light rays 101 can be in a spectrum that is either visible or invisible to the human eye. The spectrum of the light emitted from the scintillation layer 102 depends on the particular composition of the selected scintillation layer 102. The light is shown as light rays 101 passing through an amorphous silicon layer 108 on a hardened substrate 110 that supports the MEMS scanners (MEMS TFTs) 106. The hardened substrate 110 can be substantially parallel to the glass layer 104. The MEMS flat panel detector 100 includes a MEMS control module 152 and a readout electronics module 150. The MEMS control module 152 is coupled to each MEMS scanner 106 and controls linear actuators in two orthogonal directions for pivoting (illustrated at 107) about one or two orthogonal axes and producing different scan raster patterns (including rectangular raster patterns 122a, 122b, 122c and spiral raster patterns 120), such as those shown in FIG. 5B, discussed above. Exemplary embodiments of MEMS scanners 200, 300 are illustrated diagrammatically in FIGS. 9 and 10 and are discussed below. The MEMS scanners 106 included in the MEMS flat panel detector 100 can be different, including for example different type of photodiodes with different sensitivity, including pin diodes and avalanche photodiodes. Additionally, the MEMS scanners 106 can be selected to detect different light spectra emitted from different scintillation layers 102. The MEMS scanners can be positioned at different distances, such as sufficiently close together to create an area of overlap 103 between adjacent MEMS scanners 106, or sufficiently spaced apart so there is no overlap between adjacent MEMS scanners 106. In this regard, a particular area of interest can be swept by two different types of photodiodes having different sensitivities (such as avalanche photodiodes and standard photodiodes), or simply for oversampling the same region with two photodiodes having the same sensitivity. Accordingly, areas of particular interest can be imaged with resolution controlled by selected sampling rates of the ADC and provide flexibility and creativity in image processing.

Additional embodiments 100a, 100b, 100c of the MEMS flat panel detector 100 of the present teachings are described below in reference to FIGS. 6-8, highlighting the differences without repeating the description of similar features.

Figure 6:
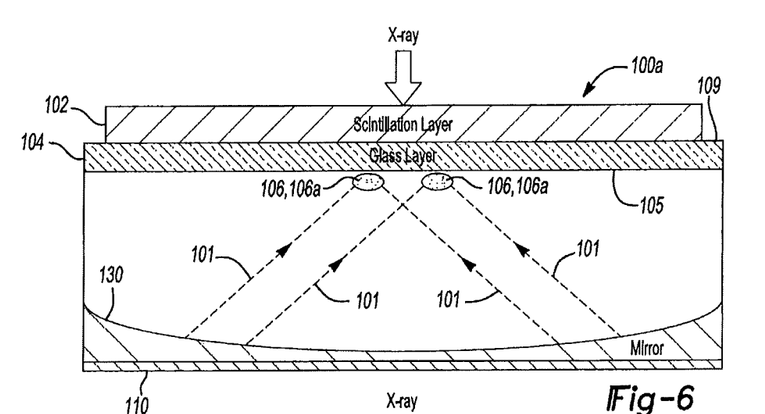
FIG. 6 is a schematic side sectional view of another embodiment of a flat panel detector according to the present teachings.

Referring to FIG. 6, another embodiment of a MEMS flat panel detector 100a is illustrated according to the present teachings. In this embodiment, the MEMS scanners 106 (106a) can be attached under the glass layer 104, on the inner surface 105 of the glass layer 104 opposite the outer surface 109 on which the scintillation layer 102 is deposited. The x-rays pass through the scintillation layer 102 as in the embodiment of FIG. 5, but the-light photons from the scintillation layer 102 hit a mirror surface 130 attached to a substrate 110 of the MEMS flat panel detector 100a, and are reflected such that reflected light rays 101 are detected by the MEMS micro-scanners 106a. The reflected light rays 101 can avoid any shadowing that can be caused by placing the MEMS scanners 106a directly under the glass layer 104. The mirror surface 130 can be concave facing the MEMS scanners 106a. In particular, the mirror surface 130 can be shaped to direct all or most of the reflected light rays 101 toward the MEMS scanners 106a and avoid losses from the edges of the MEMS flat panel detector 100a.

Figure 7:
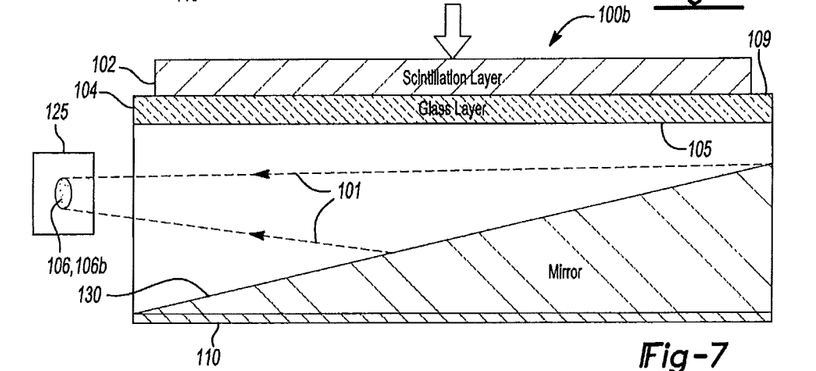
FIG. 7 is a schematic side sectional view of another embodiment of a flat panel detector according to the present teachings.

Referring to FIG. 7, another embodiment of a MEMS flat panel detector 100b is illustrated according to the present teachings. In this embodiment, one or more MEMS scanners 106 (106b) are positioned on a side panel 125 of the MEMS flat panel detector 100b, on one side and outside an area between the glass layer 104 and the mirror surface 130. The mirror surface 130 can be shaped to direct reflected light rays 101 toward the side MEMS scanners 106b. The mirror surface 130 is shown as an inclined planar surface attached to a substrate 110 in the exemplary embodiment of FIG. 7. The side placement of the MEMS scanners 106b can simplify manufacturing of the MEMS flat panel detector 100b and can facilitate scanning and control of end regions of the area of interest. It should be appreciated that the embodiments of FIGS. 6 and 7 can be combined, such that the MEMS flat panel detector includes both side MEMS scanners 106b and under the glass MEMS scanners 106a with corresponding shaping of the mirror surface 130 for directing reflected light to both locations of the MEMS scanners 106b and 106a.

Figure 8:
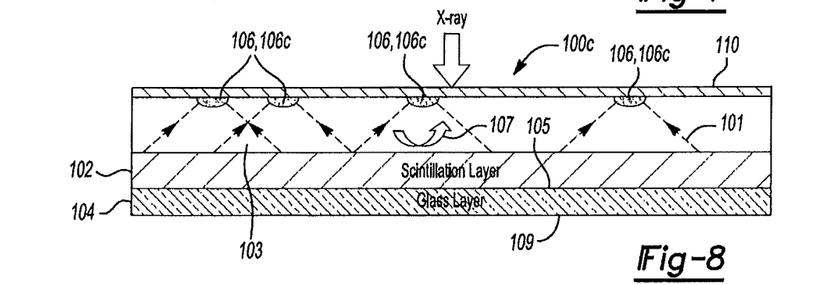
FIG. 8 is a schematic side sectional view of another embodiment of a flat panel detector according to the present teachings.

Referring to FIG. 8, another embodiment of a MEMS flat panel detector 100c is illustrated according to the present teachings. In this embodiment, one or more MEMS scanners 106 (106c) are positioned on an x-ray penetrable substrate 110 in the direct path of x-rays passing through the subject and above the scintillation layer 102 that is attached to the inner surface 105 of the glass layer 104. In this embodiment, the x-rays pass through the substrate 110 and hit the scintillation layer 102, which then glows and emits light rays 101. The light rays 101 are then detected by the MEMS scanners 106c and processed as described before in reference to FIGS. 5A and 5B.

Referring to FIGS. 9 and 10, exemplary embodiments 200, 300 of the MEMS scanners 106 referenced in FIGS. 5-8 are shown diagrammatically. Referring to FIG. 9, the MEMS scanner 200 can include a photodetector in the form of a photodiode 206 with a lens 204. The lens 204 can be a wide angle divergent lens or a fixed focal length converging lens or any other lens selected for a particular application. A sheath or mask 202 which can also be used to protect the lens 204 and/or narrow or optimize the field of view. The photodiode 206 can be mounted on a platform 208 which is movable supported on a substrate, such as, for example, on the substrate 110 of the flat panel detector 100 of FIG. 5A or other surface the MEMS scanner 200 can be mounted according to the previously described embodiments of the MEMS flat panel detectors 100, 100a 100b, 100c. In the embodiment of FIG. 9, the movement of the platform 208 can be effected by a universal pivot or hinge 220, a pair of x-axis actuators 210 and a pair of y-axis actuators 210' (not shown, but aligned orthogonally to the platform 208 perpendicular to the plane of FIG. 9). The x- and y-actuators 210, 210' can be activated via elongated connectors 212 by a corresponding MEMS control module, such as the MEMS control module 152 shown in FIG. 5A. The actuators 210, 210' can be activated with pulse signals transmitted through the connectors 212 and allow the platform to pivot about two orthogonal axes (x and y axes). The platform 208 can be actuated to move in a predefined pattern, such as, for example, a rectangular or square raster scan of specific frequency or a spiral scan, as shown in FIG. 5B. The area of the footprint of the MEMS scanners 200 can be of the order of millimeter square while the MEMS flat panel detector has dimensions of the order of 30×40 or 40×40 $cm^2$.

Referring to FIG. 10, another embodiment of a MEMS scanner 300 is illustrated. The MEMS scanner includes a disk-shaped mirror 330 that can oscillate relative to first and/or second (x and y axes). The mirror 330 can be supported on a frame 320 with flexible elements 322. The frame 320 can include a thin flexible magnetic layer and can be supported by flexible elements 318 on columns 314 through springs 316. The columns 314 can extend from a fixed substrate or from portions of a core 310 around which an electrocoil is wound forming a flux generator. Alternating current can be provided through ports P1 and P2 and induce a magnetic field. The resulting forces can rotate the frame 320 about the x axis and the mirror 330 about the y-axis relative to the frame 320. The frame 320 can be placed at a small offset relative to the center of the electrocoil for providing a net torque. Details for of MEMS scanner using a mirror are provided, for example, in Yalcinkaya et al, "NiFe Plated Biaxial MEMS Scanner for 2-D Imaging", IEEE Photonics Technology Letters, Vol. 19, No. 5, Mar. 1, 2007, pp. 330-332, which is incorporated herein by reference. Various mirror-based MEMS scanners are commercially available, for example, from Microvision, Redmond, Wash., USA.

Summarizing, the present teachings provide various MEMS flat panel detectors 100, 100a, 100b, 100c for x-ray based imaging, including CBCT imaging of patients. The MEMS flat panel detectors can include a plurality of identical or different MEMS scanners 106 in a two-dimensional array (including MEMS scanners of 200, 300) that can be actuated to provide various different scan patterns at a plurality of selected locations, including locations designed to provide overlapping fields of view and overlapping scans, to customize scanning, change resolution, control signal to noise ratio and speed of acquisition. Further, image processing can be improved by scanning the same area with two different gains from different MEMS scanners 106 having areas of overlap 103. Accordingly, the MEMS flat panel detectors of the present teachings can simplify manufacturing and provide flexibility in image scanning of areas of interest, cost reduction, reduction in calibration and image processing.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. A system comprising:
   a scintillation layer configured to (i) receive x-rays emitted from an x-ray source, and (ii) convert the x-rays to light;
   a plurality of microelectromechanical scanners configured to (i) detect corresponding portions of the light, and (ii) generate respective signals;
   a scanning module configured to actuate each of the plurality of microelectromechanical scanners, wherein each of the signals is generated based on actuation of the corresponding one of the plurality of microelectromechanical scanners; and
   a processor configured to generate an image based on the signals, wherein each of the signals contributes to a corresponding portion of the image.

2. The system of claim 1, wherein the plurality of microelectromechanical scanners comprise a plurality of transistors.

3. The system of claim 1, wherein:
   the plurality of microelectromechanical scanners comprise respectively a plurality of photodetectors;
   the plurality of photodetectors comprise a plurality of platforms; and
   the scanning module is configured to move each of the plurality of platforms.

4. The system of claim 3, wherein the scanning module is configured to:
   select a plurality of patterns; and
   move each of the plurality of platforms in a corresponding one of the plurality of patterns.

5. The system of claim 4, wherein the plurality of patterns include a spiral pattern, a radial pattern, a circular pattern, or a rectangular pattern.

6. The system of claim 1, wherein the scanning module is configured to move one of the plurality of microelectromechanical scanners at different sweep frequencies.

7. The system of claim 1, wherein:
   the plurality of microelectromechanical scanners comprise a first microelectromechanical scanner and a second microelectromechanical scanner; and
   the scanning module is configured to move (i) the first microelectromechanical scanner at a first sweep frequency, and (ii) the second microelectromechanical scanner at a second sweep frequency.

8. The system of claim 1, further comprising a plurality of mechanical actuators, wherein:
   the plurality of microelectromechanical scanners comprise respectively a plurality of photodiodes; and
   the scanning module is configured to move the plurality of microelectromechanical scanners, via the plurality of mechanical actuators, to pivot each of the plurality of photodiodes about two corresponding orthogonal axes.

9. The system of claim 1, further comprising:
   the x-ray source, wherein the x-ray source is configured to emit the x-rays toward an object; and
   a panel detector that comprises the scintillation layer and the plurality of microelectromechanical scanners, wherein the panel detector is (i) positioned on an opposite side of the object than the x-ray source, and (ii) configured to receive the x-rays after the x-rays have passed through the object.

10. The system of claim 1, further comprising a second layer disposed between the scintillation layer and the plurality of microelectromechanical scanners.

11. The system of claim 10, wherein:
the second layer is configured to receive the light from the scintillation layer; and
the plurality of microelectromechanical scanners are configured to receive the light after the light has passed through the second layer.

12. The system of claim 11, further comprising a mirror, wherein the plurality of microelectromechanical scanners are disposed between the second layer and the mirror such that the plurality of microelectromechanical scanners are configured to receive the light after the light has reflected off of the mirror.

13. The system of claim 1, further comprising a second layer and a third layer, wherein:
the second layer comprises the plurality of microelectromechanical scanners, wherein the x-rays pass through the second layer and are then received at the scintillation layer;
the scintillation layer is disposed between the second layer and the third layer; and
the plurality of microelectromechanical scanners are configured to receive the light after the light has been emitted from the scintillation layer.

14. The system of claim 1, wherein the plurality of microelectromechanical scanners are configured to detect corresponding portions of the light and generate the respective signals.

15. A system comprising:
a scintillation layer configured to (i) receive x-rays emitted from an x-ray source, and (ii) convert the x-rays to light;
a plurality of transistors configured to (i) detect corresponding portions of the light, and (ii) generate respective signals;
a scanning module configured to actuate each of the plurality of transistors, wherein each of the signals is generated based on actuation of the corresponding one of the plurality of transistors; and
a processor configured to generate an image based on the signals, wherein each of the signals contributes to a corresponding portion of the image.

16. The system of claim 15, wherein the scanning module is configured to:
select a plurality of patterns; and
move each of the plurality of transistors in a corresponding one of the plurality of patterns.

17. The system of claim 16, wherein the one or more patterns includes a spiral pattern, a radial pattern, a circular pattern or a rectangular pattern.

18. The system of claim 15, wherein the scanning module is configured to move one of the plurality of transistors at different sweep frequencies.

19. The system of claim 15, wherein:
the plurality of transistors comprise a first transistor and a second transistor; and
the scanning module is configured to move (i) the first transistor at a first sweep frequency, and (ii) the second transistor at a second sweep frequency.

20. The system of claim 15, further comprising a plurality of mechanical actuators, wherein
the scanning module is configured to move the plurality of transistors, via the plurality of mechanical actuators, to pivot each of the plurality of transistors about two corresponding orthogonal axes.

21. The system of claim 15, further comprising:
the x-ray source configured to emit the x-rays toward an object; and
a panel detector that comprises the scintillation layer and the plurality of transistors, wherein the panel detector is (i) positioned on an opposite side of the object than the x-ray source, and (ii) configured to receive the x-rays after the x-rays have passed through the object.

22. The system of claim 15, further comprising a glass layer disposed between the scintillation layer and the plurality of transistors.

23. The system of claim 22, wherein:
the glass layer is configured to receive the light from the scintillation layer; and
the plurality of transistors are configured to receive the light after the light has passed through the glass layer.

24. The system of claim 23, further comprising a mirror, wherein the plurality of transistors are disposed between the glass layer and the mirror such that the plurality of transistors are configured to receive the light after the light has reflected off of the mirror.

25. The system of claim 15, further comprising a silicon layer and a glass layer, wherein:
the silicon layer comprises the plurality of transistors, wherein the x-rays pass through the silicon layer and are then received at the scintillation layer;
the scintillation layer is disposed between the silicon layer and the glass layer; and
the plurality of transistors are configured to receive the light after the light has been emitted from the scintillation layer.

26. A method comprising:
providing a scintillation layer;
receiving x-rays emitted from an x-ray source at the scintillation layer;
converting the x-rays to light via the scintillation layer;
detecting corresponding portions of the light via a plurality of photodiodes;
generating signals based on the detected portions of the light via the plurality of photodiodes;
actuating each of the plurality of photodiodes, wherein each of the signals is generated based on the actuating of the corresponding one of the plurality of photodiodes; and
generating an image based on the signals, wherein each of the signals contributes to a corresponding portion of the image.

27. The method of claim 26, wherein:
actuating the plurality of photodiodes comprises actuating a plurality of platforms; and
the plurality of photodiodes are mounted on the plurality of platforms.

28. The method of claim 27, further comprising:
selecting a plurality of patterns; and
moving each of the plurality of platforms in a corresponding one of the plurality of patterns.

29. The method of claim 26, further comprising moving one of the plurality of photodiodes at different sweep frequencies.

30. The method of claim 26, further comprising:
moving a first photodiode at a first sweep frequency; and
moving a second photodiode at a second sweep frequency, wherein the plurality of photodiodes comprise the first photodiode and the second photodiode.

31. The method of claim 26, further comprising moving the plurality of photodiodes, via a plurality of mechanical actuators, to pivot each of the plurality of photodiodes about two corresponding orthogonal axes.

32. The method of claim 26, wherein the x-rays are emitted from the x-ray source and toward an object and are received by the plurality of photodiodes after the x-rays have passed through the object.

33. The method of claim 26, further comprising providing a second layer disposed between the scintillation layer and the plurality of photodiodes, wherein:
   the light is received from the scintillation layer at the second layer; and
   the light is received at the plurality of photodiodes after the light has passed through the second layer.

34. The method of claim 26, further comprising providing:
   a second layer disposed between the scintillation layer and the plurality of photodiodes; and
   a mirror,
   wherein
      the light is received from the scintillation layer at the second layer,
      the light is received at the plurality of photodiodes after the light has passed through the second layer,
      the plurality of photodiodes are disposed between the second layer and the mirror, and
      the light is received at the plurality of photodiodes after the light has reflected off of the mirror.

35. The method of claim 26, further comprising providing:
   a second layer; and
   a third layer disposed between the scintillation layer and the plurality of photodiodes,
   wherein
      the second layer comprises the plurality of photodiodes,
      the x-rays pass through the second layer and are then received at the scintillation layer,
      the scintillation layer is disposed between the second layer and the third layer, and
      the light is received at the plurality of photodiodes after the light has been emitted from the scintillation layer.

* * * * *

UNITED STATES PATENT AND TRADEMARK OFFICE
CERTIFICATE OF CORRECTION

PATENT NO.      : 9,883,840 B2                                  Page 1 of 1
APPLICATION NO. : 14/611509
DATED           : February 6, 2018
INVENTOR(S)     : Barbato et al.

It is certified that error appears in the above-identified patent and that said Letters Patent is hereby corrected as shown below:

In the Specification

Column 3, Line 44, Detailed Description, Line 16: Delete "((two-dimensional" and insert --(two-dimensional-- therefore;

Column 8, Line 31, Detailed Description, Line 4: Delete "subject" and insert --patient-- therefore;

Column 11, Line 24, Detailed Description, Line 7: After "electrocoil", insert --332-- therefore;

Column 11, Line 27, Detailed Description, Line 9: Delete "x axis" and insert --x-axis-- therefore; and Column 11, Line 29, Detailed Description, Line 11: After "electrocoil", insert --332--.

Signed and Sealed this
Eighth Day of May, 2018

Andrei Iancu
*Director of the United States Patent and Trademark Office*